United States Patent
Dotta

(10) Patent No.: US 7,854,322 B2
(45) Date of Patent: Dec. 21, 2010

(54) FACILITATED FAST-OPENING PACKAGING OF PLASTER AND METHOD OF MANUFACTURING

(76) Inventor: Angelo Dotta, Via Alamandini No. 10-1, Bologna (IT) 40136

( * ) Notice: Subject to any disclaimer, the term of this patent is extended or adjusted under 35 U.S.C. 154(b) by 0 days.

(21) Appl. No.: 11/910,538

(22) PCT Filed: Apr. 3, 2006

(86) PCT No.: PCT/IB2006/051001
§ 371 (c)(1),
(2), (4) Date: Oct. 3, 2007

(87) PCT Pub. No.: WO2006/106468
PCT Pub. Date: Oct. 12, 2006

(65) Prior Publication Data
US 2008/0191003 A1 Aug. 14, 2008

(30) Foreign Application Priority Data
Apr. 4, 2005 (IT) ............................... TO05A0217

(51) Int. Cl.
*A61L 15/00* (2006.01)
(52) U.S. Cl. .......................... 206/441; 206/440; 602/57
(58) Field of Classification Search ................ 206/441, 206/440; 602/41, 57
See application file for complete search history.

(56) References Cited

U.S. PATENT DOCUMENTS

| 2,017,819 | A | * | 10/1935 | Rohlfing | .................. 229/87.06 |
| 2,969,145 | A | * | 1/1961 | Hannauer, Jr. | .............. 206/441 |
| 3,018,881 | A | * | 1/1962 | Wall | ........................... 206/441 |
| 4,235,337 | A | | 11/1980 | Dotta | |
| 4,418,822 | A | | 12/1983 | Dotta | |
| 4,598,004 | A | | 7/1986 | Heinecke | |
| 4,837,062 | A | * | 6/1989 | Dunshee et al. | ............ 428/41.3 |

(Continued)

FOREIGN PATENT DOCUMENTS

GB 833437 A 4/1960

OTHER PUBLICATIONS

International Search Report for PCT/IB2006/051001, dated Sep. 6, 2006.

*Primary Examiner*—Mickey Yu
*Assistant Examiner*—Jenine M Pagan
(74) *Attorney, Agent, or Firm*—Sughrue Mion, PLLC

(57) ABSTRACT

The present invention refers to a fast-opening plaster packaging comprising a plaster having at least an adhesive support protected with at least two films (P1, P2) made of protective material and detachable from the adhesive support, and an envelope (E) suitable for containing the plaster. The envelope has at least two portions (E1, E2) mutually dividable and each dividable portion of the envelope is anchored to at least one of the protective films (P1, P2). The packaging is characterized in that at least one of the protective films (P1, P2) has at least a cut (I1, I2) suitable for shaping one or more columns and one or more arcades (LA) or semi-arcades. The column(s) is(are) joined to the corresponding semi-wrapper (E1) at anchoring line (C1) of the protective film (P1) and is(are) able, upon pulling at least one of the portions (E1) of the envelope (E), to fold onto itself(themselves) as such one or more arcades or semi-arcades (LA) made of protective material are substantially not involved into folding.

12 Claims, 3 Drawing Sheets

U.S. PATENT DOCUMENTS

| | | | |
|---|---|---|---|
| 4,915,102 A * | 4/1990 | Kwiatek et al. | 604/307 |
| 5,074,293 A | 12/1991 | Lott et al. | |
| 5,162,040 A | 11/1992 | Annett | |
| 5,266,371 A | 11/1993 | Sugii et al. | |
| 5,275,284 A | 1/1994 | Onotsky | |
| 6,010,002 A | 1/2000 | Petterson | |
| 6,124,521 A | 9/2000 | Roberts | |
| 6,140,549 A * | 10/2000 | Pompei, Jr. | 602/57 |
| 6,719,137 B2 | 4/2004 | Dotta | |
| 6,923,320 B2 | 8/2005 | Grossman | |
| 7,012,170 B1 * | 3/2006 | Tomaioulo | 602/57 |
| 2002/0195367 A1 | 12/2002 | Dotta | |
| 2004/0004014 A1 * | 1/2004 | Grossman | 206/440 |

\* cited by examiner

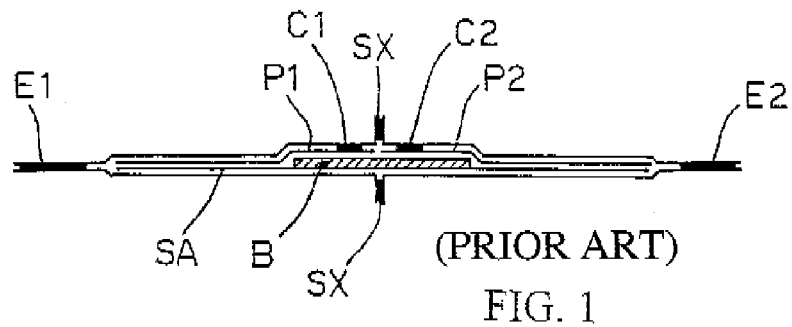
(PRIOR ART)
FIG. 1
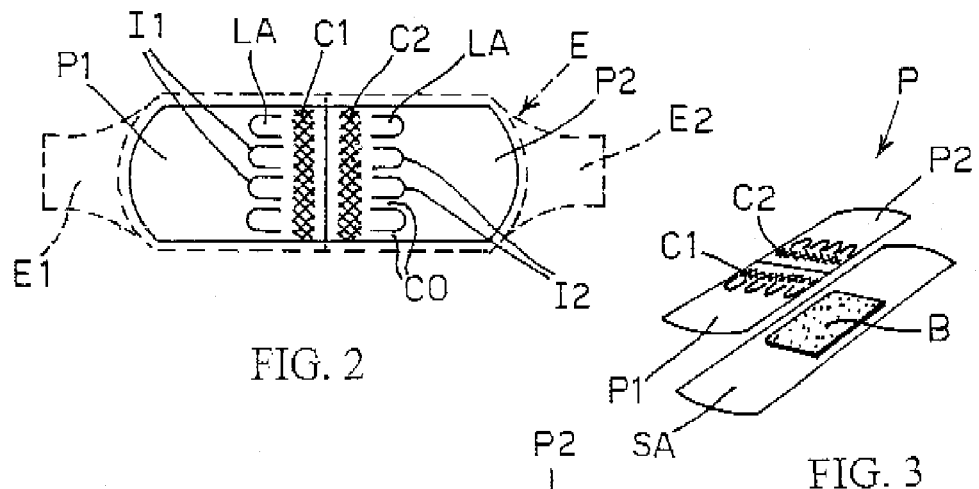
FIG. 2
FIG. 3
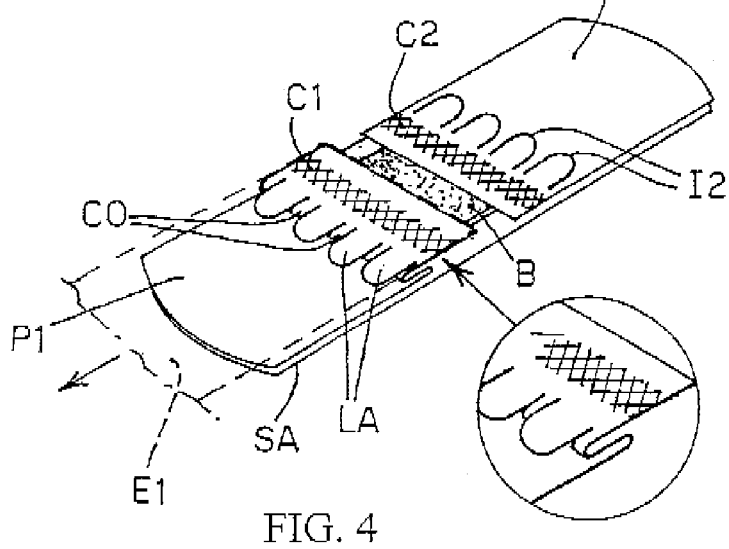
FIG. 4

FACILITATED FAST-OPENING PACKAGING OF PLASTER AND METHOD OF MANUFACTURING

CROSS REFERENCE TO RELATED APPLICATIONS

This application is a National Stage of International Application No. PCT/IB2006/051001 filed on Apr. 3, 2006, claiming priority based on Italian Patent Application No. TO2005A000217, filed Apr. 4, 2005, the contents of all of which are incorporated herein by reference in their entirety.

TECHNICAL FIELD

The present invention refers to fast-opening packagings of plaster and to the relevant method of manufacturing.

In particular, the present invention refers to fast-opening packagings wherein the plaster comprises an adhesive support and protective films (films or protection) and wherein the films, placed onto the adhesive side of the adhesive support, are siliconated or anyway provided with anti-adhering treatment.

BACKGROUND OF THE INVENTION

Packagings of plaster allowing a fast-opening are commercially available.

Such packagings comprise a wrapper or an envelope enfolding the plaster and they are suitable for allowing the envelope fast-opening by simply pulling the envelope ends. In particular, in such kind of packagings, the ends pulling action causes the separation of the wrapper into two semi-wrappers, one of which separates from the plaster dragging with it one protective film placed onto a part of the plaster adhesive support, which thus remains mostly uncovered and ready for application; the other semi-wrapper, together with the part of covered adhesive support, is held by the user in his/her hand, so that he/she can pull it away and reveal the whole plaster in immediate sequence.

Packagings of such a kind are disclosed, for instance in U.S. Pat. No. 4,418,822 and U.S. Pat. No. 4,235,337 in the name of the applicant.

U.S. Pat. No. 4,418,822 discloses, for instance, a packaging of plasters wherein the protective films of the adhesive support are attached to the respective semi-wrappers with a lip folded towards outside.

U.S. Pat. No. 4,235,337 discloses protective films of the adhesive support having a direct back anchor to the respective semi-wrappers.

The technical solution disclosed in U.S. Pat. No. 4,418,822 substantially concerns non-siliconated protective films.

The technical solution disclosed in U.S. Pat. No. 4,235,337 substantially concerns siliconated or anyway provided with anti-adhering treatment protective films, in case obtainable also from support material (liner) employed for the manufacturing of the plasters adhesive support.

A problem that is particularly felt with respect to the second known solution resides in that, as it can be deduced by looking at FIG. 1 depicting a longitudinal schematic section of the packaging according to the second known solution, a considerable pulling action has to be exerted on ends E1, E2 in order to open the package, since the strength to separate the semi-wrappers joined one to the other at median lines SX (cold self-welding paper) has to be added to the strength required by one of the films P1, P2 to fold onto itself, for instance as an S or as a Z, and to start detaching an initial portion of the film from the adhesive side (adhesive), a strength that in the case of FIG. 1 is made easier thanks to the presence of a bandage compress B isolating a large part of the initial portion of films P1, P2 from the adhesive.

Moreover, the applicant has noticed that, due to the required strength, it can happen, for instance, that the films initial portions, instead of folding onto themselves, tend to bend or to deviate from the desired folding so that the user is induced to exert an even greater pulling strength, that can result in a wrong opening of the packaging.

SUMMARY OF THE INVENTION

It is an object of the present invention to make much more easier the folding of the protective films onto themselves and, consequently, to reduce the overall strength for opening the plaster packaging.

It is also an object of the present invention to provide a relatively simple and very cheap solution that can be applied to the usual components of the protective films, the use of liner obtained from the adhesive support not being excluded.

The objects are achieved with the fast-opening packaging of plaster having the features referred to in the following claims.

The present invention further relates to a method for the manufacturing of plasters to be used in connection with the packagings according to the invention.

The claims form integral part of the technical teaching herein provided as regards the invention.

According to a preferred embodiment, it is provided that the plaster protective film comprises a cut having a "portico" profile, designed and arranged so that, under the pulling strength, the folding and the removal of the films only involve the "columns" of the portico (i.e. a largely minority portion of the region of the films themselves), particularly in the initial portion of the opening of the plaster packaging that, as it is known, is simultaneous to the mutual detachment of the semi-wrappers forming the envelope. This way the initial strength, that is the one by far prevailing in the opening step of the plaster packaging, is significantly reduced, also because the portico cut of the film causes a guided folding, which mainly takes place along the track preset by the cut, avoiding unwanted flexions or deviations of the protective film.

According to a further feature of the present invention, the protective film cut is shaped in a way such as to assure that, during a first opening step of the plaster packaging, the strength is substantially related to the mutual detachment of the semi-wrappers because the films, having a minimum surface subjected to folding, for instance one or more columns, have minimum resistance to opening and that, during a second step, once the semi-wrappers are separated, the opening strength of the packaging is substantially related to the films folding.

DESCRIPTION OF THE FIGURES

This and other features of the present invention will become evident from the following description of preferred embodiments, given by way of non limiting example, the enclosed drawings being of help, in which elements denoted with the same or with a similar alphanumeric reference denote components having the same or a similar function and design:

FIG. 1 depicts a longitudinal schematic section of a plaster packaging according to the prior art as disclosed;

FIG. 2 depicts a view from the side of the protective film of a plaster packaging according to the invention;

FIG. 3 depicts a perspective exploded view of the plaster according to the invention;

FIG. 4 depicts a perspective exploded view exemplifying the opening of the plaster packaging according to the invention;

DESCRIPTION OF PREFERRED EMBODIMENTS

With reference to FIG. 2, a fast-opening packaging of plaster according to the invention comprises, for instance, a wrapper (envelope) E enfolding a plaster P (FIG. 2, FIG. 3) having an adhesive support SA, of a known kind, and protective films, P1 and P2, arranged, in a known way, onto the adhesive side of the adhesive support SA.

Wrapper E comprises, for instance, two semi-wrappers, E1 and E2, of a known kind, and the protective films, P1 and P2, have the ends placed at the center line (median ends) of the plaster P sticked, in a known way, through respective sticking strips (stickings or anchor lines), C1 and C2, to the respective semi-wrappers, E1 and E2.

Plaster P also comprises, for instance, a bandage compress (compress) B, known in itself, located in median place, and the protective films, P1 and P2, cover and protect, in a known way, the compress B.

Protective films, P1 and P2, are for instance made of a protective material of a known kind, for instance consisting of or comprising siliconated paper.

According to a first embodiment, the protective films, P1 and P2, have a transverse set of cuts (carvings), I1 and I2, for instance cuts as an U, that placed side by side form a "portico" pattern suitable for shaping columns CO and arcade tabs (arches or arcades) LA on the protective films P1 and P2. Preferably, columns CO are much narrower than arches LA.

In such first embodiment, the arches LA tops of P1 and P2 are substantially based onto the transverse edges of compress B.

When using, by pulling towards outside the end of the semi-wrappers, E1 and E2, (FIG. 2, FIG. 3, FIG. 4) thanks to the sticking C1, the carving I1 of P1 overlying compress B, is able to split open into the two components shaped by cutting, whereby the arcade tabs LA, having a high resistance to folding, slide, together with the semi-wrapper E1, on the underlying compress B and on the portion of P1 not engaged by compress B, while the columns CO, having a low resistance to folding, fold onto themselves substantially outlining an S or a Z.

This step of folding onto themselves of the columns CO is simultaneous to the step of mutual detachment of the semi-wrappers, E1 and E2, composing the envelope; afterwards, keeping on pulling, the detachment of the portion of P1, fully engaged by the adhesive itself, from the adhesive of the adhesive support SA takes place. Such detachment occurs without any difficulty, through columns CO acting as sheer pulling braces, also because, at this point, the envelope E is already open and it does not impart a considerable resistance to sliding and to folding onto itself of the uncut portion of films P1 and P2.

Figure 5:
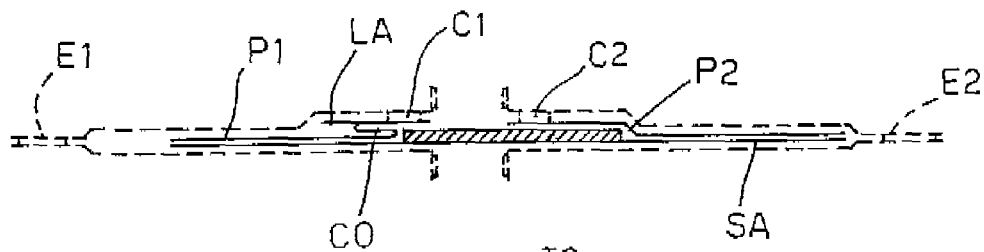
FIG. 5 depicts a longitudinal schematic section of a semi-open packaging of a plaster according to the invention.

In order to better exemplify the opening process of the plaster packaging according to such first embodiment, FIG. 5 illustrates an enlarged schematic longitudinal section of a semi-open packaging of a plaster, in which the dotted lines denote the contours of the semi-wrappers E1 and E2 already separated.

As highlighted in such figure, the arcade tabs LA completely project with respect to the folded columns CO and these latters are stretched like braces ready to start pulling the side of P1 that is in contact with the adhesive of the adhesive support SA. As it is easy to understand for the person skilled in the art, it is intuitive that, keeping on pulling, the removal of P1 will require a minimum strength, such as not to break the columns or braces CO, also because the mouth of the semi-wrapper E1 anchored to P1 through the sticking strip C1 is open, as already cited above.

In short, thanks to the carvings, during a first step the opening strength of the plaster packaging is substantially related to the mutual detachment of the semi-wrappers E1 and E2, since the films P1 and/or P2, having a minimum surface subjected to folding, for instance the columns, have minimum resistance to opening.

During a second step, once the semi-wrappers are separated, the opening strength of the plaster packaging is substantially related to the folding of the films P1 and/or P2.

Figure 6:
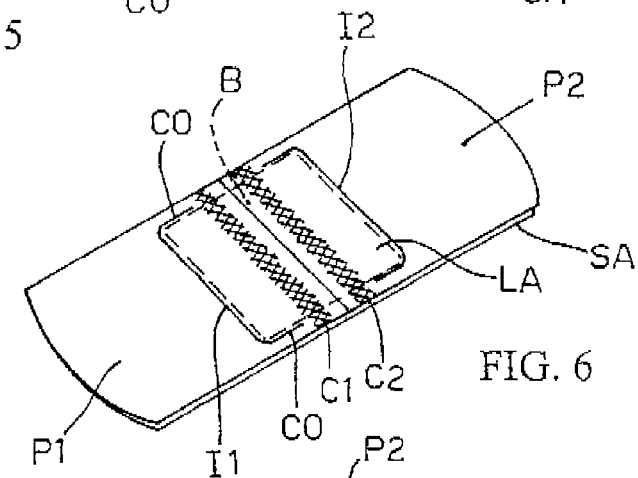
FIG. 6 depicts a view from the side of the protective film of a plaster according to a second embodiment of the invention.

In a second embodiment, each of the films, P1 and P2 (FIG. 6), comprises a cut, I1 and I2 respectively, as an U suitable for shaping a portico (first portion) with an arch LA having a width equal or similar, for instance, to that of compress B, and just two lateral columns CO (second portion); in such second embodiment, the bandage compress B substantially supports the whole portion of the protection, P1 and/or P2, delimited by the portico cut.

Such kind of shape involves that the first portion of protection, being slightly raised over the second portion, which on the contrary is engaged by the adhesive, does not meet any difficulty to slide on the bandage compress B when, during use, a pulling action of the protective films, P1 and P2, is exerted beginning from the sticking strips C1 and C2.

Obviously, as it is easy to understand for the person skilled in the art, columns CO will fold onto themselves as an S or as a Z, performing the same functions already disclosed as regards columns CO of the first embodiment.

Figure 7:
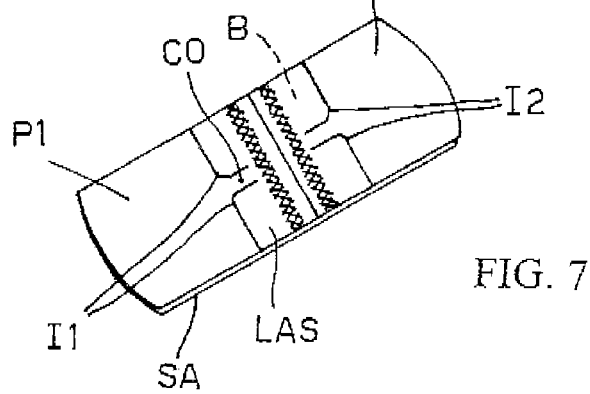
FIG. 7 depicts a view from the side of the protective film of a plaster according to a third embodiment of the invention.

In a third embodiment, the protective films, P1 and P2 (FIG. 7), comprise cuts, I1 and I2, suitable for shaping two semi-arcades LAS and a single middle column CO. Such kind of embodiment, that is anyway comprised within the protective scope of the present invention, can be preferable for plasters P provided with bandage compresses B extended up to the edges of the adhesive support SA.

According to a fourth embodiment, usable for instance for packagings wherein plaster P is of the without bandage kind, the protective films, P1 and P2 (FIG. 8), may comprise, respectively, portico cuts I1 and I2 with the arcades facing the median ends of the protective films, P1 and P2, of plaster P.

Figure 8:
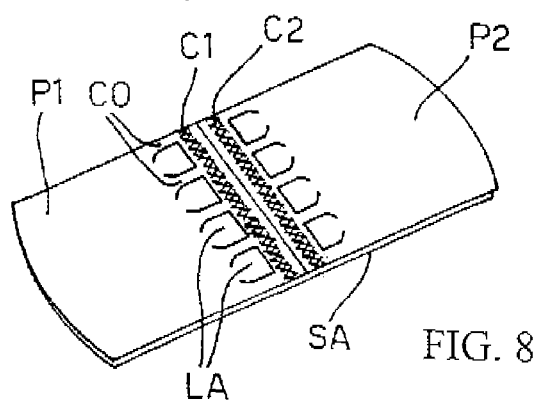
FIG. 8 depicts a view from the side of the protective film of a plaster according to a fourth embodiment of the invention.

Making reference to FIG. 8, it can be deduced, as it is easy to understand for the person skilled in the art, that, by exerting a pulling action of the film P1 starting, for instance, from the sticking strip C1, the column CO will tend to detach from the underlying adhesive support SA folding onto themselves, while the arcade tabs LA will remain anchored to the adhesive support until columns CO will be entirely overturned onto themselves and stretched like braces to transmit the pulling action to the arcade tabs LA themselves. The tearing removal of the arcade tabs LA will require a determined strength, generally higher than that provided in the case of the first embodiment, whereby, in this fourth embodiment, an enlargement of columns CO base is provided, for instance giving the portico cuts a horseshoe profile, so as to strengthen them and to avoid breakings.

In such embodiment, it is preferable that the protective films are, for instance, made of a material such as siliconated plastics or the like that, as it is known, is less stiff and tearable of the siliconated paper.

In such embodiment, furthermore, it is preferable that the region of the protective films, P1 and P2, that comprises the respective sticking lines or strips, C1 and C2, is treated, for instance, by embossing or knurling, so to slightly raise such region over the surface of the adhesive support SA and to help the columns CO folding (which takes place just under such region) and, anyway, so as to facilitate the initial tearing detachment of the region itself from the adhesive.

In the examples so far considered, tabs made of unremoved protective material are provided near the columns, because said material is not cut at the arcades base; however, the removal of the material corresponding to the arcades can result of some advantage for plasters provided with a wide bandage compress, as long as the underlying surface of the bandage compress corresponds to the empty space so created.

The method of manufacturing of the plaster packaging according to the invention, according to the disclosed different embodiments, is as follows.

During a first step, the protective material under the form of a ribbon, for instance rolled up into rolls R (FIG. 9), is made to pass, in a known way, between a cutting-die F and a counter-roller CC before applying the material itself onto the adhesive support.

The rotary cutting-die F will comprise, for instance, cutters T shaped according to one of the carving shapes I1, I2, illustrated in the disclosed different embodiments.

Therefore, during such first step, the ribbon, passing between the rotary cutting-die F and the counter-roller CC, will receive the cutters T print and will then have, for instance, a set of portico cuts producing one of the shapes of columns CO and arcade tabs LA as disclosed.

Figure 9:
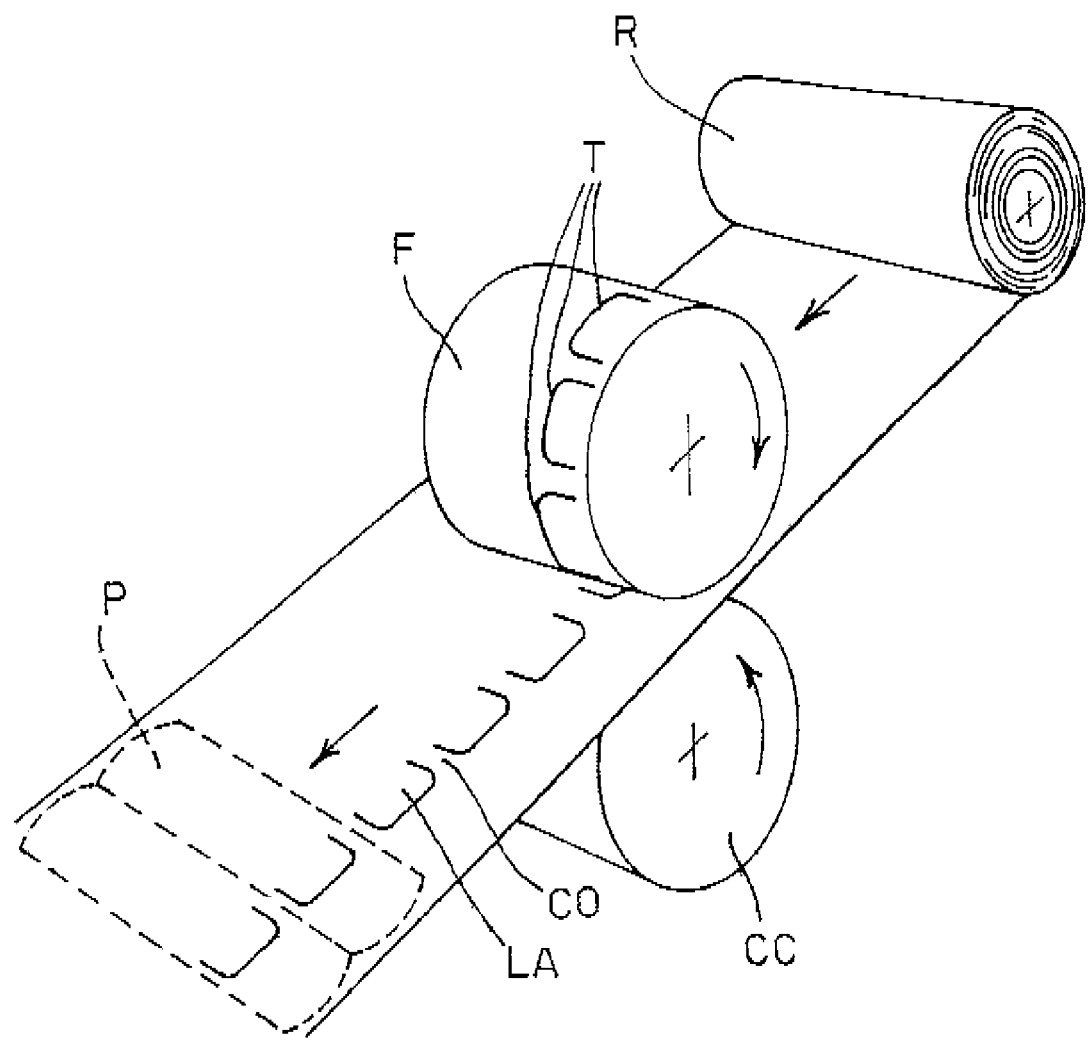
FIG. 9 depicts an example of device to be used in the method of manufacturing of the plasters according to the invention.

During a second step, once coupled the protective material with the adhesive support, the final pattern on the protective films of plaster P, which in FIG. 9, merely illustrative, corresponds to the second embodiment, will be obtained, for instance, by a die-cutting manufacture of the single plasters.

Within the present description, to denote the interruptions of the protective material upon which the invention is based, the wording "cut" or "carving" are used that nevertheless, as it is easy to understand for the person skilled in the art, are not to be understood in a limiting way, since they are used for brevity's sake.

Within the present description, "cut" and "carving" mean, for instance, any interruption of the protective material anyway obtained, also by removing a minimum of material (e.g. by laser) or by considerably removing (by melting, by cutting out). This specification is intended to be valid in all respects for interpreting the following claims, to which is better to declare beforehand also that the proposed alternatives and solutions within this description are illustrative only and are not to be understood to be exhaustive regards the subject matter for which protection is claimed. This last specification concerns, as well, the sizes that can be deduced from the drawings, which in the different possible accomplishments can considerably change, also among them, thus producing for instance protective films having different lengths for the same plaster, separable wrappers dividing into unequal envelopes, cuts having different profiles from a film to another one and so on, in fact, obvious changes or alternatives to the above description are possible, in sizes, shapes, materials, components, as well as in the details of the illustrated construction and of the method of manufacturing without departing from the spirit of the invention as specified by the following claims.

The invention claimed is:

1. A packaging comprising:
   an adhesive support protected with at least two films made of flexible protective material wherein the at least two films are detachable from said adhesive support; and
   an envelope comprising two semi-wrappers mutually dividable by pulling an end of each of the two semi-wrappers away from each other;
   wherein the two semi-wrappers are stuck to a respective one of the at least two films;
   wherein at least one of the at least two films comprises at least one cut that forms a corresponding at least one tab, wherein the at least one tab is spaced apart from an edge of one of the at least two films that faces another one of the at least two films; and
   wherein a width of the at least one tab comprises a majority of the width of one of the at least two films.

2. The packaging according to claim 1, wherein the tab extends away from the abutting edge of one of the at least two films.

3. The packaging according to claim 1, wherein the at least one cut is a "U" shaped cut forming at least one column and the at least one tab.

4. The packaging according to claim 3, wherein the at least one column is joined to a corresponding semi-wrapper at a sticking strip of the protective film.

5. The packaging according to claim 3, wherein the at least one column is configured to bend when the two semi-wrappers are separated and wherein the at least one tab is configured to remain straight when the two semi-wrappers are separated.

6. The packaging according to claim 1, wherein the adhesive support is partially covered by a bandage compress.

7. The packaging according to claim 1, wherein the packaging is a facilitated fast-opening packaging of plaster.

8. The packaging according to claim 1, wherein the at least one tab comprises only one tab.

9. The packaging according to claim 1, wherein the at least one tab comprises a plurality of tabs such that the combined width of the plurality of tabs comprises a majority of the width of the one of the at least two films.

10. A packaging comprising:
    an adhesive support protected with at least two films made of flexible protective material wherein the at least two films are detachable from said adhesive support; and
    an envelope comprising two semi-wrappers mutually dividable by pulling an end of each of the two semi-wrappers away from each other;
    wherein the two semi-wrappers are stuck to a respective one of the at least two films;
    wherein at least one of the at least two films comprises a plurality of discontinuous cuts that form a plurality of columns and a plurality of tabs, wherein the columns are configured to bend when the semi-wrappers are pulled away from each other and the tabs are configured to remain straight when the semi-wrappers are pulled away from each other.

11. The packaging according to claim 10, wherein the plurality of tabs are spaced apart from an edge of one of the at least two films that faces another one of the at least two films.

12. The packaging according to claim 10, wherein a sum of a width of the plurality of tabs comprise a majority of the width of one of the at least two films.

* * * * *